United States Patent
Nishimura et al.

(10) Patent No.: US 9,885,645 B2
(45) Date of Patent: Feb. 6, 2018

(54) THERMAL ANALYZER

(71) Applicant: Hitachi High-Tech Science Corporation, Minato-ku, Tokyo (JP)

(72) Inventors: Shinya Nishimura, Tokyo (JP); Hirohito Fujiwara, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 343 days.

(21) Appl. No.: 14/657,141

(22) Filed: Mar. 13, 2015

(65) Prior Publication Data
US 2015/0260665 A1 Sep. 17, 2015

(30) Foreign Application Priority Data

Mar. 14, 2014 (JP) .................... 2014-051829
Dec. 12, 2014 (JP) .................... 2014-251649

(51) Int. Cl.
*G01N 5/04* (2006.01)

(52) U.S. Cl.
CPC ...................... *G01N 5/04* (2013.01)

(58) Field of Classification Search
CPC ........................................... G01N 5/04
See application file for complete search history.

(56) References Cited

U.S. PATENT DOCUMENTS

| 6,257,757 B1 | 7/2001 | Nakamura |
| 7,500,779 B2 | 3/2009 | Takeuchi et al. |
| 2005/0123020 A1* | 6/2005 | Nakamura ............... G01N 5/04 374/14 |
| 2006/0140246 A1* | 6/2006 | Danley ................. G01G 19/52 374/14 |
| 2007/0201533 A1 | 8/2007 | Takeuchi et al. |
| 2012/0307864 A1* | 12/2012 | Blumm .............. G01N 25/4806 374/158 |
| 2013/0235899 A1 | 9/2013 | Nagasawa et al. |

FOREIGN PATENT DOCUMENTS

| JP | H07-23257 U | 4/1995 |
| JP | H07-146262 A | 6/1995 |
| JP | H11-326249 A | 11/1999 |
| JP | 2005-331432 A | 12/2005 |
| JP | 2007-232479 A | 9/2007 |
| JP | 2013-185834 A | 9/2013 |

* cited by examiner

*Primary Examiner* — Lisa Caputo
*Assistant Examiner* — Punam Roy
(74) *Attorney, Agent, or Firm* — Banner & Witcoff, Ltd.

(57) ABSTRACT

A thermal analyzer is provided with: a furnace tube; a sample holder; a heating furnace; a measurement chamber; and a measurement unit. The heating furnace comprises a fixing section to be fixed to the furnace tube. The furnace tube is configured to be attachable to and detachable from the heating furnace and provided with an engagement portion that is configured to be engaged with the fixing section at a variable position in the radial direction. A gap jig is configured to be detachable from the heating furnace and the furnace tube after inserting the furnace tube into the heating furnace and engaging the engagement portion of the furnace tube with the fixing section while the gap jig is interposed between the heating furnace and the furnace tube to maintain the gap between the heating furnace and the furnace tube in the radial direction to be in the predetermined distance.

8 Claims, 12 Drawing Sheets

Related Art

THERMAL ANALYZER

CROSS-REFERENCE TO RELATED APPLICATION

This application claims priority from Japanese Patent Application No. 2014-051829, filed on Mar. 14, 2014, and from Japanese Patent Application No. 2014-251649, filed on Dec. 12, 2014 the entire subject matters of which are incorporated herein by reference.

BACKGROUND

1. Technical Field

The present invention relates to a thermal analyzer for measuring a physical change in a sample with a temperature change caused by heating the sample.

2. Description of the Related Art

Conventionally, as a technique of evaluating temperature characteristics of a sample, there has been employed a technique called thermal analysis for measuring a physical change of a sample along with its temperature change caused by heating the sample. A definition of thermal analysis can be found in JIS K 0129: 2005 "General rules for thermal analysis," and thermal analysis, according to this definition, includes all techniques that measure the physical properties of a measurement target (sample) under program controlled temperatures. Five common thermal analysis methods are (1) Differential Thermal Analysis (DTA) that detects temperatures (temperature difference), (2) Differential Scanning calorimetry (DSC) that detects a heat flow difference, (3) Thermogravimetry (TG) that detects masses (weight change), (4) Thermomechanical Analysis (TMA) and (5) Dynamic Mechanical Analysis (DMA) that detect mechanical properties.

Figure 9:
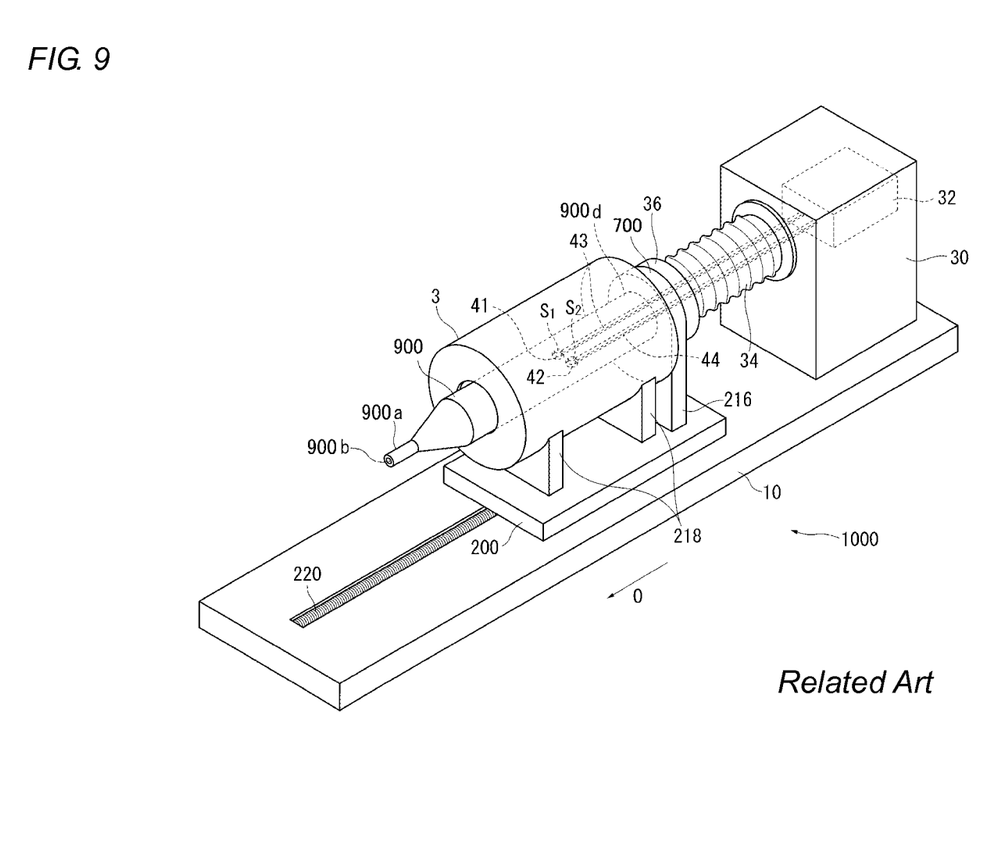
FIG. 9 is a perspective view illustrating a thermogravimetry (TG) apparatus according to a related art.

The thermal analyzer 1000 shown in FIG. 9 represents a known example of thermal analyzers. The thermal analyzer 1000 performs Thermogravimetry (TG), and, as required, Differential Thermal Analysis (DTA). This thermal analyzer is provided with: a furnace tube 900 which is formed in a cylindrical shape and has an outlet 900b, which is reduced in diameter, on a anterior end portion 900a; a cylindrical heating furnace 3 which surrounds the furnace tube 900 from the outside; sample holders 41 and 42 which are arranged in the furnace tube 900 and hold samples $S_1$ and $S_2$ via sample containers; a measurement chamber 30 which is connected air tight to a posterior end portion 900d of the furnace tube 900; and a weight detector 32 which is arranged inside the measurement chamber 30 to measure weight changes in the samples (cf. JP-A-11-326249, JP-A-2007-232479, and JP-A-7-146262). The thermal analyzer also includes: two supporting pillars 218 extending downward from the lower end of the heating furnace 3. The supporting pillars 218 are connected to a support base 200. A flange 700 is fixed to the outside of the posterior end portion 900d of the furnace tube 900, and a single supporting pillar 216 extends downward from the lower end of the flange 700. The supporting pillar 216 is also connected to the support base 200. The support base 200 and the measurement chamber 30 are mounted on a base 10. The support base 200 is allowed to advance and retreat in an axial direction O of the furnace tube 900 by a linear actuator 220.

The heating furnace 3 heats the sample holders 41 and 42 from outside of the furnace tube 900, and the weight detector 32 detects the weights of the samples $S_1$ and $S_2$ as they change with temperature.

Figure 10:
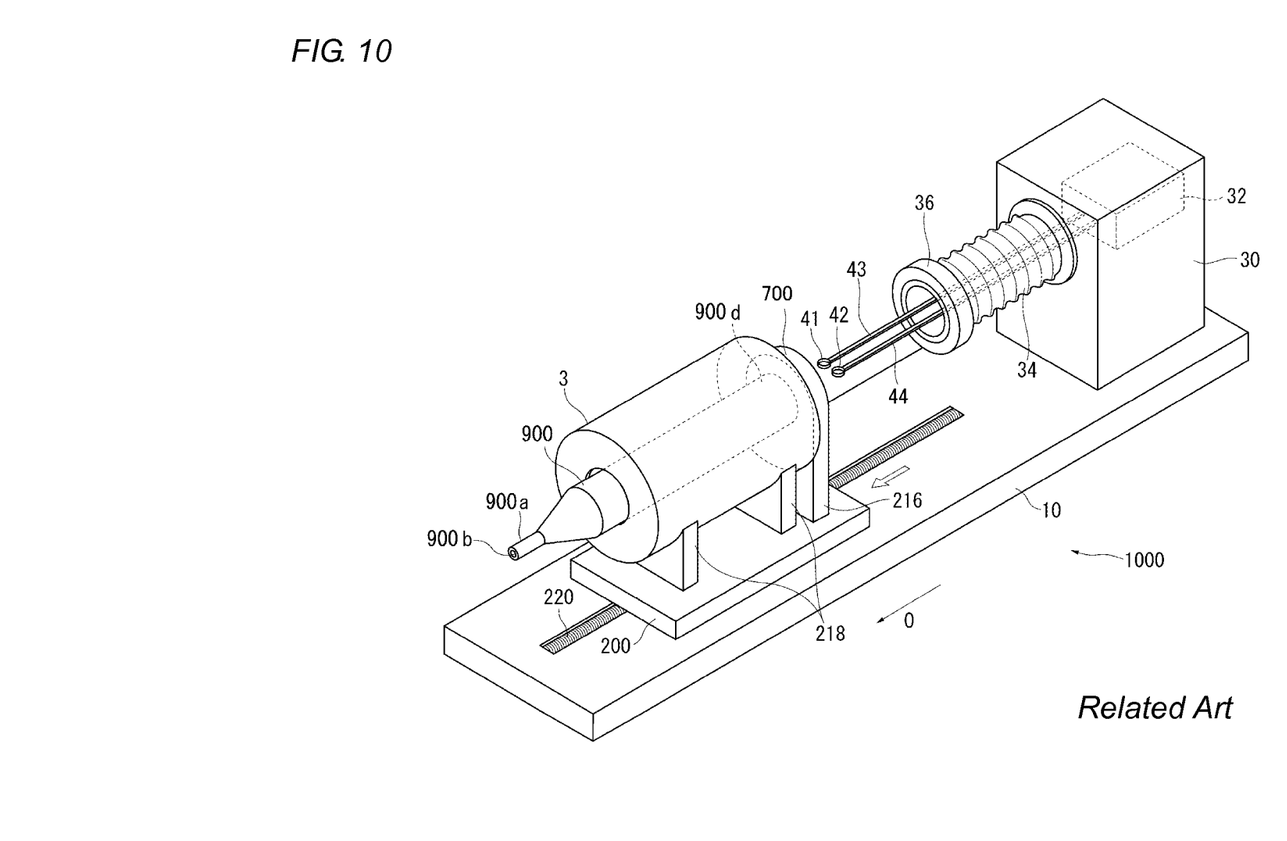
FIG. 10 is a view illustrating a mode in which a sample is set in the thermogravimetry (TG) apparatus or replaced according to the related art.

Here, as illustrated in FIG. 10, when the samples $S_1$ and $S_2$ are to be set on the sample holders 41 and 42 or the samples $S_1$ and $S_2$ are to be replaced, the support base 200 is allowed to advance toward the front end side (to the left in FIG. 10) of the furnace tube 900 by the linear actuator 220 so as to allow the heating furnace 3 and the furnace tube 900 fixed to the support base 200 to advance. Accordingly, the sample holders 41 and 42 are exposed on a side closer to the rear end side than the furnace tube 900, and thus the samples $S_1$ and $S_2$ can be set therein or replaced.

However, when the thermal analyzer described above is used, although a desired thermophysical property value can be detected, there is a problem in that changes in the samples during thermal analysis cannot be visually observed. This is because the furnace tube 900 is generally formed of ceramics such as sintered alumina or heat-resistant metal such as Inconel (registered trademark) and the heating furnace 3 covers the furnace tube 900.

With respect to these conventional thermal analyzers, the Applicants of the present application have proposed, in US patent publication No. US 2013/235899 A1, a new thermal analyzer that includes a furnace tube formed of a transparent material, and in which the furnace tube is exposed by moving forward only the heating furnace for sample observation so that a sample can be observed from outside of the exposed furnace tube. It is also proposed in US 2013/235899 A1 to cover a part of the exposed furnace tube with a heat conducting member, and partially inserting the heat conducting member into the heating furnace to transfer the heat of the heating furnace to the exposed furnace tube, and maintain the sample in a heated state at the sample observation position.

However, since a quartz glass tube, a YAG ceramic tube, or the like is used as the transparent furnace tube described in US 2013/235899 A1, as a result of repeated measurement at a high temperature (for example, near 1100° C.), a loss of clarity may occur. Particularly, in a case where a quartz glass tube which is relatively cheap is used as the furnace tube, the loss of clarity becomes significant. In addition, when the clarity of the furnace tube is deteriorated, observation of the sample is impeded, and thus the furnace tube needs to be replaced.

In order to make uniform the heat distribution or heat conduction of the furnace tube in the heating furnace, the furnace tube and the heating furnace need to be concentrically fixed to each other by allowing the axial centers thereof to match with each other. However, a gap needs to be provided between the inner surface of the heating furnace and the furnace tube so as not to cause the furnace tube therein to be broken due to thermal expansion of the heating furnace, and in order to secure heat conduction from the heating furnace, the gap needs to be maintained at a low value of about 1.5 mm. Therefore, it is difficult to accurately maintain the gap whenever the furnace tube is replaced and to accurately fix the furnace tube to the heating furnace concentrically.

SUMMARY

The present invention has been made in view of the above-described circumstances, and one of objects of the present invention is to provide a thermal analyzer capable of, when a furnace tube formed of a transparent material is attached to or detached from a heating furnace, allowing the axial centers of the heating furnace and the furnace tube to match with each other and accurately fixing the two to each other concentrically.

According to an exemplary embodiment of the present invention, there is provided a thermal analyzer including: a furnace tube made of a transparent material in a cylindrical shape, the furnace tube having an outlet on an anterior end portion thereof in an axial direction; a sample holder that is arranged in the furnace tube and having a mounting face on which a sample container containing a measurement sample is mounted; a heating furnace configured to have a cylindrical shape and to surround the furnace tube from outside; a measurement chamber connected air-tight to the furnace tube at a posterior end portion of the furnace tube in the axial direction; a measurement unit arranged inside the measurement chamber and measures changes in physical properties of the sample; and a gap jig configured to maintain a gap between the heating furnace and the furnace tube in a radial direction to be in a predetermined distance. The heating furnace includes a fixing section to be fixed to the furnace tube. The furnace tube is configured to be attachable to and detachable from the heating furnace. The furnace tube includes an engagement portion that is configured to be engaged with the fixing section at a variable position in the radial direction. The gap jig is configured to be detachable from the heating furnace and the furnace tube after inserting the furnace tube into the heating furnace and engaging the engagement portion of the furnace tube with the fixing section while the gap jig is interposed between the heating furnace and the furnace tube to maintain the gap between the heating furnace and the furnace tube in the radial direction to be in the predetermined distance.

According to an exemplary embodiment of the present invention, there is provided a thermal analyzer includes: a furnace tube made of a transparent material in a cylindrical shape, the furnace tube having an outlet on an anterior end portion thereof in an axial direction; a sample holder that is arranged in the furnace tube and including a mounting face on which a sample container containing a measurement sample is mounted; a heating furnace configured to have a cylindrical shape and to surround the furnace tube from outside; a measurement chamber connected air-tight to the furnace tube at a posterior end portion of the furnace tube in the axial direction; and a measurement unit arranged inside the measurement chamber and measures changes in physical properties of the sample. The heating furnace includes a fixing section to be fixed to the furnace tube. The furnace tube includes, on an inner surface of the heating furnace, a protrusion configured to maintain a gap between the heating furnace and the furnace tube in a radial direction in a predetermined distance by being in contact with the furnace tube. The furnace tube includes an engagement portion that is configured to be engaged with the fixing section at a variable position in the radial direction. The engagement portion is configured to be engaged with the fixing section after inserting the furnace tube into the heating furnace and bringing the protrusion of the heating furnace into contact with an outer surface of the furnace tube to maintain the gap between the heating furnace and the furnace tube in the radial direction to be in the predetermined distance.

BRIEF DESCRIPTION OF THE DRAWINGS

The above and other aspects of the present invention will become more apparent and more readily appreciated from the following description of illustrative embodiments of the present invention taken in conjunction with the attached drawings, in which.

DETAILED DESCRIPTION

Embodiments of the present invention will be described with reference to the drawings. In the following, the term "anterior end (side)" will be used to refer to the anterior end portion 9a side of a furnace tube 9 in a direction along axial direction O, and the term "posterior end (side)" will be used to refer to the opposite side of the furnace tube 9. A surface which faces the front end side in the axial direction O is referred to as a "front end facing surface", and a surface which faces the rear end side is referred to as a "rear end facing surface".

Figure 1:
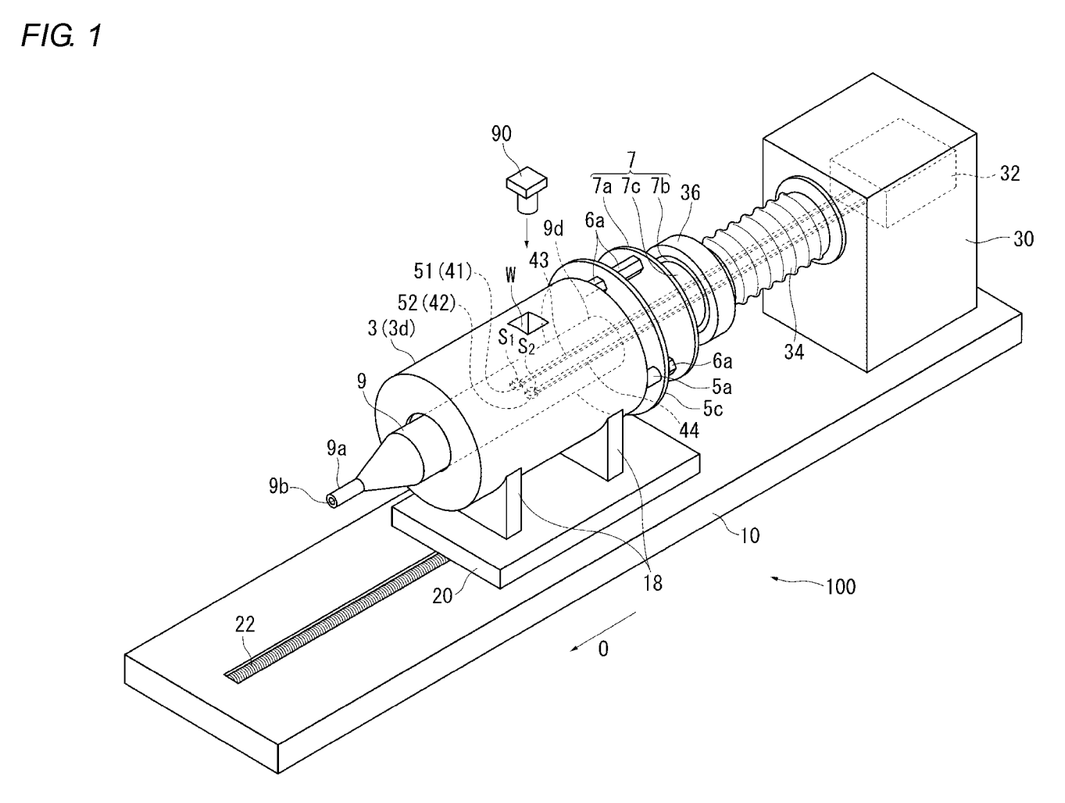
FIG. 1 is a perspective view illustrating a configuration of a thermal analyzer according to a first embodiment of the present invention.
Figure 2:
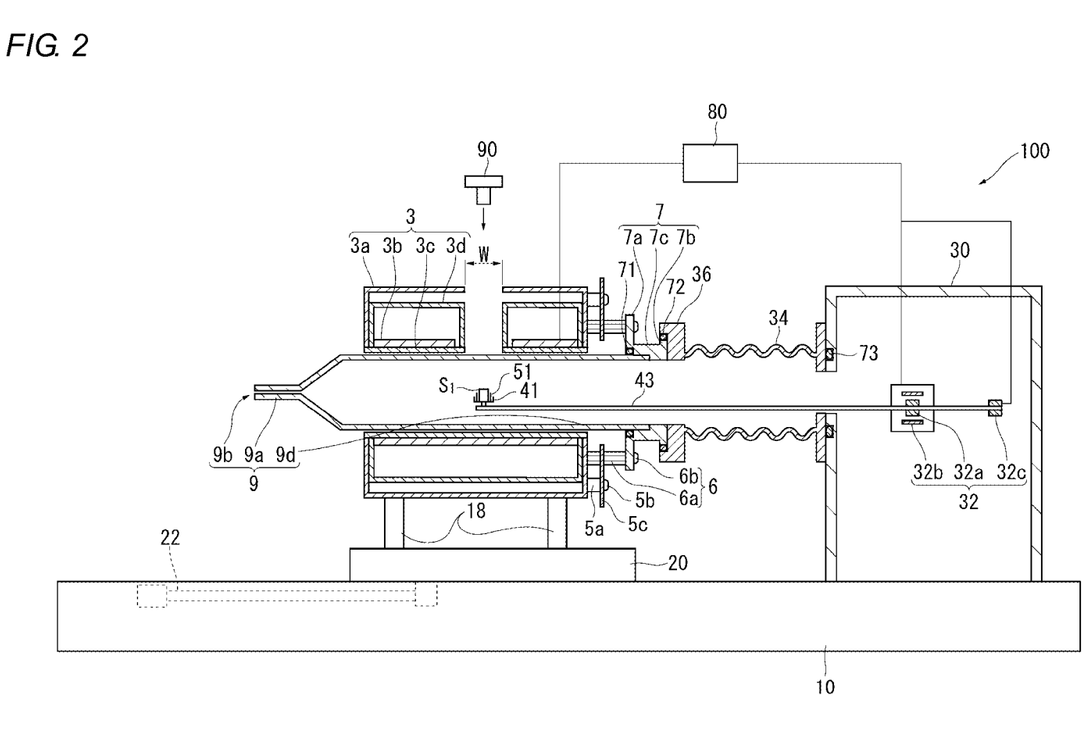
FIG. 2 is a cross-sectional view along an axial direction of the thermal analyzer.
Figure 3:
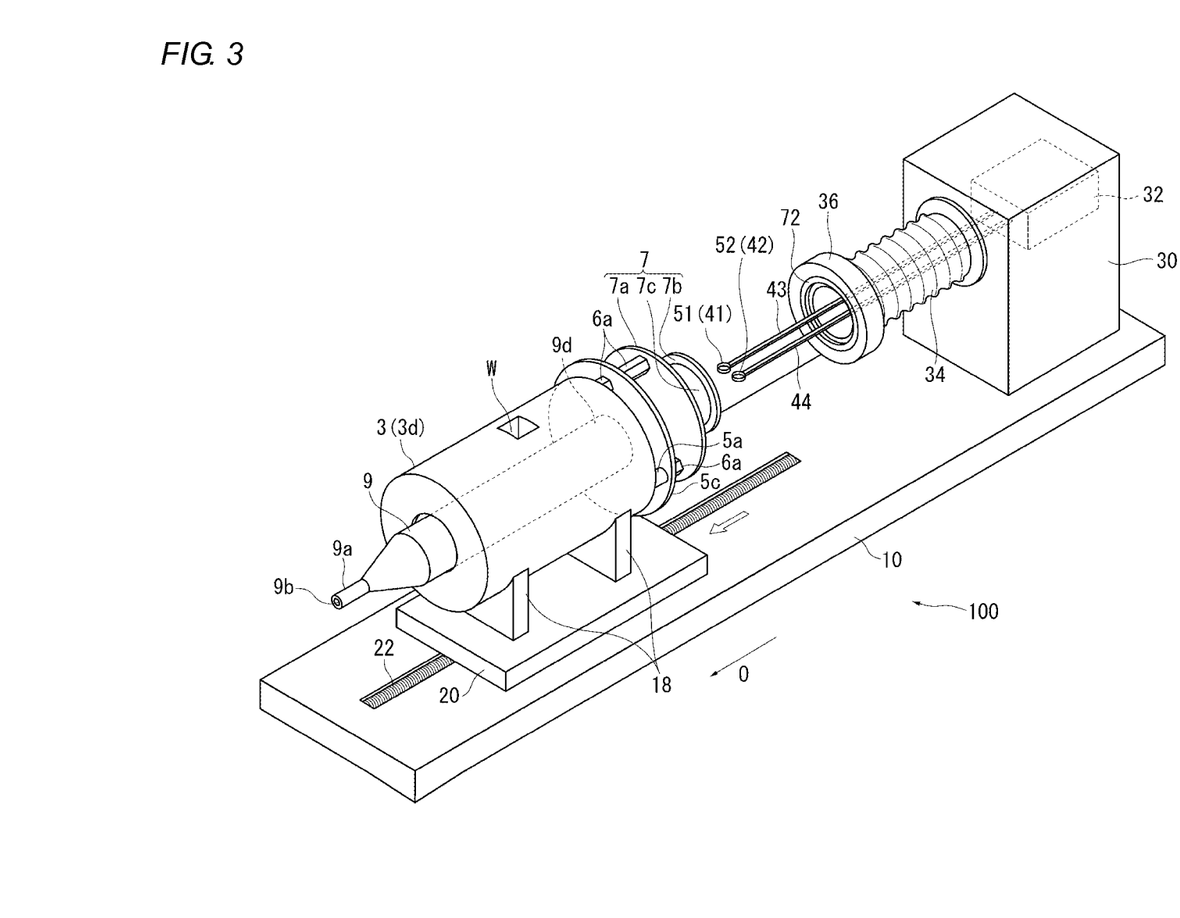
FIG. 3 is a view illustrating a mode in which a sample is set in the thermal analyzer or replaced.
Figure 4:
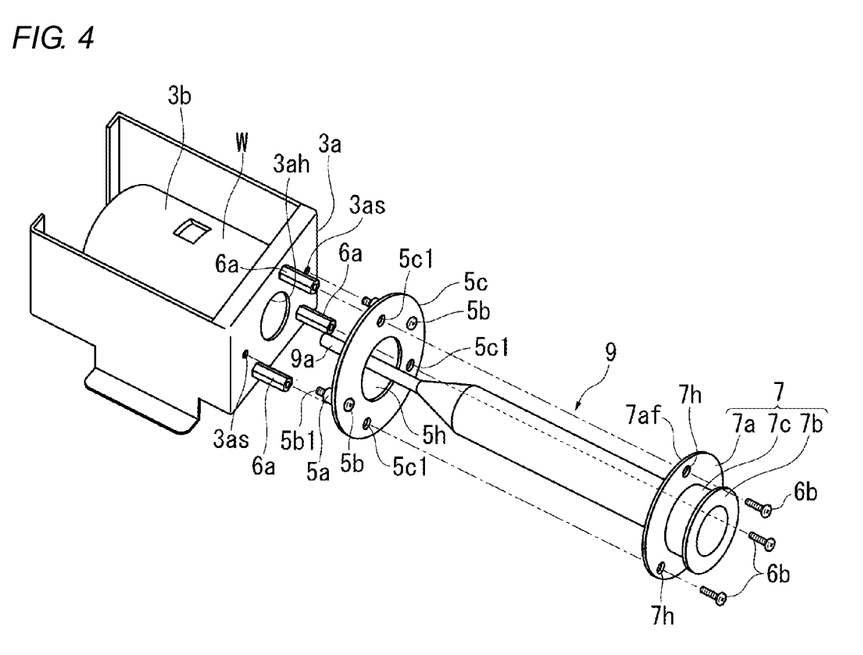
FIG. 4 is an exploded perspective view of the thermal analyzer.

FIG. 1 is a perspective view illustrating a configuration of a thermal analyzer 100 according to a first embodiment of the present invention. FIG. 2 is a cross sectional view of the thermal analyzer 100 taken in a vertical section that passes an axis of the furnace tube 9. FIG. 3 is a view illustrating a mode in which a sample is set in the thermal analyzer 100 or replaced. FIG. 4 is an exploded perspective view of the thermal analyzer 100. In addition, FIGS. 1 to 4 illustrate a state in which a gap jig, which will be described later, is detached.

The thermal analyzer 100 is configured as a thermogravimetry (TG) apparatus and is provided with: a cylindrical furnace tube 9; a cylindrical heating furnace 3 surrounding the furnace tube 9 from outside; a pair of sample holders 41 and 42 which are arranged in the furnace tube 9; a support base 20; a measurement chamber 30 connected to a posterior end portion 9d of the furnace tube 9 in the axial direction O; a weight detector 32 (corresponding to "measurement unit" in the claims) which is arranged in the measurement chamber 30 and measures weight changes in samples $S_1$ and $S_2$; and a base 10 having an upper surface on which the measurement chamber 30 is placed. The measurement sample (sample) $S_1$ and the reference sample $S_2$ are respectively accommodated in a pair of sample containers (see FIGS. 2) 51 and 52, and the sample containers 51 and 52 are respectively placed on the pair of sample holders 41 and 42. The reference sample $S_2$ is a reference material for the measurement sample.

Two supporting pillars 18 extend from the lower end of the heating furnace 3 in the vicinity of both ends thereof in the axial direction, and each of the supporting pillars 18 is connected to the upper surface of the support base 20. A flange 7 is fixed to the outside of the posterior end portion 9d of the furnace tube 9, and the flange 7 is fixed to (engaged with) the posterior end portion of the heating furnace 3 via a fixing section 6.

The base 10 has a groove formed along the axial direction O, and a linear actuator 22 is arranged in the groove. The posterior end of the linear actuator 22 is connected to the support base 20, and the anterior end (servomotor) is connected to the base 10. The support base 20 can be moved back and forth with the linear actuator 22 along the groove in the axial direction O.

The linear actuator 22 may be configured by components, for example, such as a ball screw and a servomotor, and may be configured by any known actuator capable of linear actuation along axial direction O.

The heating furnace 3 has a cylindrical furnace core tube 3c which forms the inner surface of the heating furnace 3, a heater 3b which is externally fitted to the furnace core tube 3c, a cylindrical heat shield portion 3d which covers the periphery and the side surface of the furnace core tube 3c, and a substantially rectangular housing 3a (see FIG. 2) which surrounds the heat shield portion 3d. At the centers of both side walls of the housing 3a, insertion holes 3h (see FIG. 4) through which the furnace tube 9 is inserted are provided. In FIG. 1, illustration of the housing 3a is omitted.

The heat shield portion 3d prevents radiant heat of the heater 3b from dissipating and effectively transfers the radiant heat to the furnace tube 9. The housing 3a surrounds the heat shield portion 3d to keep the heating furnace 3 warm, and an appropriate adjustment hole (not illustrated) may be provided in the housing 3a to adjust the temperature of the heating furnace 3. In addition, the inner diameter of the furnace core tube 3c is greater than the outer diameter of the furnace tube 9, and the heating furnace 3 heats the furnace tube 9 (and the samples $S_1$ and $S_2$ therein) via a predetermined gap in a contactless manner.

A substantially rectangular opening W which penetrates through the heating furnace 3 in a direction from the heat shield portion 3d to the furnace core tube 3c is formed in the upper surface of the heating furnace 3 such that the samples S1 and S2 in the furnace tube 9 can be observed and photographed via the opening W. In addition, a predetermined opening (for example, a circular hole) which overlaps the opening W is formed in the housing 3a to oppose the opening W. For example, in the examples of FIGS. 1 and 2, imaging device (for example, a camera, a digital camera, a video camera, an optical microscope, or the like) 90 is arranged above the opening W to observe the samples S1 and S2 during thermal analysis.

The furnace tube 9 is reduced in diameter in a tapered shape toward the anterior end portion 9a, and the anterior end portion 9a is formed in a long, thin capillary shape and has an open outlet 9b at the front end thereof. In addition, purge gas is appropriately introduced into the furnace tube 9 from the rear end side, and the purge gas and decomposition products of the samples due to heating are exhausted to the outside through the outlet 9b. On the other hand, the flange 7 having a ring shape is attached to the outside of the posterior end portion 9d of the furnace tube 9 via a seal member 71 (see FIG. 2).

The furnace tube 9 is formed of a transparent material such that the samples S1 and S2 can be observed from the outside of the furnace tube 9. Here, the transparent material is a material which transmits visible light at a predetermined transmittance and also includes a translucent material. As the transparent material, quartz glass, sapphire glass, or YAG (yttrium aluminum garnet) ceramic may be appropriately used.

Balance arms 43 and 44 which extend toward the rear end side in the axial direction θ are respectively connected to the sample holders 41 and 42, and the balance arms 43 and 44 are parallel to each other in the horizontal direction. Immediately below the sample holders 41 and 42, thermocouples are installed to measure the sample temperatures. The balance arms 43 and 44 and the sample holders 41 and 42 are formed of, for example, platinum.

In this embodiment, as the balance arms 43 and 44, two parallel balance arms respectively corresponding to the measurement sample and the reference sample are used. However, depending on the method of setting a reference, the reference sample may become unnecessary. In this case, only a single balance arm may be used for the measurement sample.

The measurement chamber 30 is arranged at the rear end of the furnace tube 9, and a tubular bellows 34 that extends toward the furnace tube 9 in a direction toward the front end side in the axial direction O is attached to the anterior end portion of the measurement chamber 30 via a seal member 73. The front end side of the bellows 34 forms a flange portion 36, and the flange portion 36 is connected air tight to the flange 7 via a seal member 72. In this manner, the measurement chamber 30 and the inside of the furnace tube 9 communicate with each other, and the rear end of each of the balance arms 43 and 44 extends to the inside of the measurement chamber 30 through the furnace tube 9. As the seal members 71 to 73, for example, an O-ring, a gasket, or the like may be used.

As illustrated in FIG. 2, the weight detector 32 arranged in the measurement chamber 30 includes coils 32a, magnets 32b, and position detection units 32c. The position detection unit 32c is configured as, for example, a photosensor and is arranged at the rear end side of each of the balance arms 43 and 44 to detect whether or not the balance arms 43 and 44 are in a horizontal state. The coil 32a is attached to the center (fulcrum) of each of the balance arms 43 and 44 in the axial direction, and the magnets 32b are arranged on both sides of the coil 32a. In addition, current is supplied and flows through the coil 32a to allow the balance arms 43 and 44 to become horizontal, and by measuring the current, the weight of each of the samples S1 and S2 at the front ends of the balance arms 43 and 44 are measured. In addition, the weight detector 32 is provided for each of the balance arms 43 and 44.

As illustrated in FIG. 2, the linear actuator 22, the heater 3b, and the weight detector 32 are controlled by a controller 80 configured by, for example, a computer. Specifically, the controller 80 controls current flow to the heater 3b and heats the samples $S_1$ and $S_2$ set in the sample containers 51 and 52 by heating the furnace tube 9 according to a predetermined heating pattern. At this time, the differential heat and the sample temperatures of the corresponding samples $S_1$ and $S_2$ are acquired by the thermocouples arranged immediately below the sample holders 41 and 42, and weight changes in the samples are acquired from the weight detector 32. In addition, the controller 80 controls the operation of the linear actuator 22 to move the heating furnace 3 and the furnace tube 9 to a measurement position and a sample setting position, which will be described later. As described above, the flange portion 36 and the flange 7 are connected air tight to each other, and thermal analysis is performed at a position where the heating furnace 3 covers each of the sample holders 41 and 42 (that is, the samples $S_1$ and $S_2$) of the furnace tube 9.

FIG. 3 illustrates the positions of the heating furnace 3 and the furnace tube 9 in a case where the samples $S_1$ and $S_2$ are respectively set in the sample containers 51 and 52 on the sample holders 41 and 42 or replaced. In the case where the samples $S_1$ and $S_2$ are set (arranged) in the sample containers 51 and 52 or replaced, when the support base 20 is allowed to advance toward the front end side (to the left in FIG. 3) of the furnace tube 9 by the linear actuator 22, the furnace tube 9 and the heating furnace 3 which are fixed to the support base 20 advance toward the front end side from the measurement position, and thus the sample holders 41 and 42 are exposed on a side closer to the rear end side than the furnace tube 9 and the heating furnace 3. Accordingly, the samples $S_1$ and $S_2$ can be set in the sample containers 51 and 52 or replaced.

As described above, at a position where the flange portion 36 and the flange 7 are separated from each other in the axial direction O and the sample holders 41 and 42 (that is, the samples S1 and S2) are exposed on a side closer to the rear end side than the furnace tube 9 and the heating furnace 3, setting in the sample containers or replacing of the samples is performed.

Next, fixing of the furnace tube 9 to the heating furnace 3, which is a feature of the present invention will be described with reference to FIGS. 4 to 7.

Figure 7A:
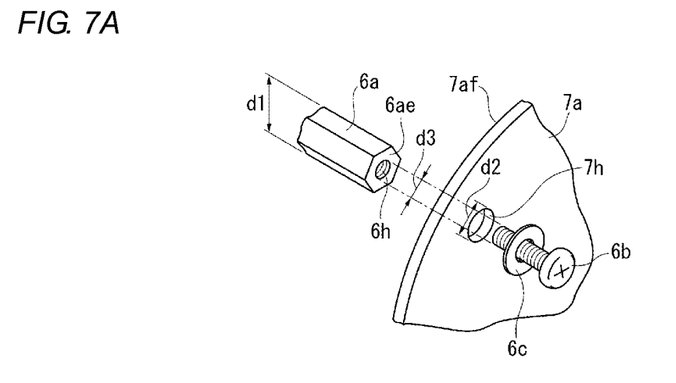
FIGS. 7A and 7B are views illustrating a mode in which an engagement portion is engaged with a fixing section.
Figure 7B:
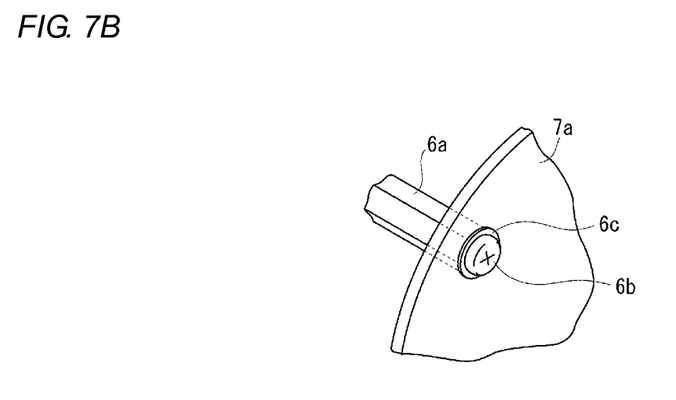

As illustrated in FIG. 4, a plurality of (in this embodiment, three) rods 6a having a hexagonal columnar shape extend toward the rear end side from the rear end of the heating furnace 3 (the housing 3a). Here, the three rods 6a surround the periphery of the furnace tube 9 and are arranged on the same circumference at equal intervals (at circumferential angles of 120 degrees) on a side closer to the inside in the radial direction than a heat shield plate 5c, which will be described later. As illustrated in FIGS. 7A and 7B, screw holes 6h are open to a rear end facing surface 6ae of the rod 6a, and a male screw 6b is screwed into the screw hole 6h via a washer 6c.

The rod 6a, the male screw 6b, and the washer 6c correspond to the "fixing section" 6 in the claims.

The flange 7 is formed to have a substantially H-lettered shape when viewed in a direction perpendicular to the axial direction (see FIG. 2) and has a shape in which a first flange 7a having an annular shape positioned on the front end side, a second flange 7b having an annular shape positioned on the rear end side, and a cylindrical connection portion 7c are integrally connected in the axial direction. In addition, the flange 7 having the ring shape is attached to the outside of the posterior end portion 9d of the furnace tube 9 via the seal member 71. The inner surface of the flange 7 is reduced in diameter in a stepped shape toward the rear end side from the front end side, and when the furnace tube 9 is inserted into the flange 7 from the front end side thereof, the rear end facing surface of the furnace tube 9 abuts the stepped portion of the inner surface of the flange 7 and is fixed into the flange 7.

The first flange 7a has a greater diameter than that of the second flange 7b, surrounds the periphery of the furnace tube 9, and extends outward in the radial direction from (the circumference of) the rods 6a. In addition, at three positions of the first flange 7a respectively corresponding to the rods 6a, bolt holes 7h are formed. The first flange 7a corresponds to an "engagement portion" in the claims.

As illustrated in FIG. 2, a recessed portion in which the second flange 7b is accommodated is formed in the front end facing surface of the flange portion 36 which faces the second flange 7b, and the seal member 72 is arranged along the inner surface of the recessed portion. When the second flange 7b is inserted into the recessed portion, the seal member 72 comes into close contact with the outer peripheral surface of the second flange 7b used for sealing.

Figure 5A:
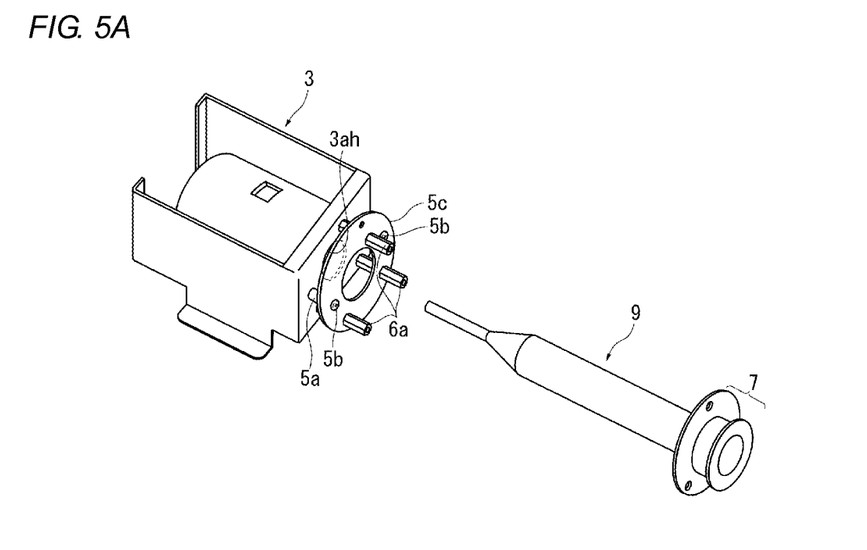
FIGS. 5A and 5B are views illustrating a mode in which a furnace tube is fixed to a heating furnace using gap jigs.
Figure 5B:
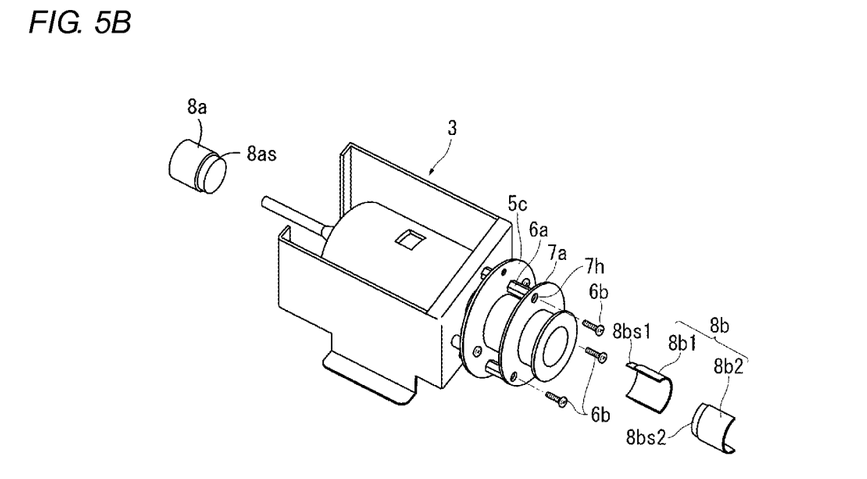

As illustrated in FIGS. 5A and 5B, the furnace tube 9 is inserted through the insertion hole 3h of the rear end side of the heating furnace 3 (the housing 3a). At this time, as illustrated in FIGS. 7A and 7B, a front end facing surface 7af of the first flange 7a is allowed to abut the rear end facing surface 6ae of the rod 6a, and the male screw 6b is screwed into the rod 6a from a rear end facing surface Tae of the first flange 7a via the bolt hole 7h such that the first flange 7a is engaged with the rod 6a. Accordingly, the furnace tube 9 is fixed to the heating furnace 3 (the housing 3a). When the furnace tube 9 is detached from the heating furnace 3 (the housing 3a), in the reverse order, the male screw 6b may be unscrewed from the rod 6a and the furnace tube 9 may be extracted from the insertion hole 3h of the rear end side of the heating furnace 3 (the housing 3a) toward the rear end side.

Figure 6:
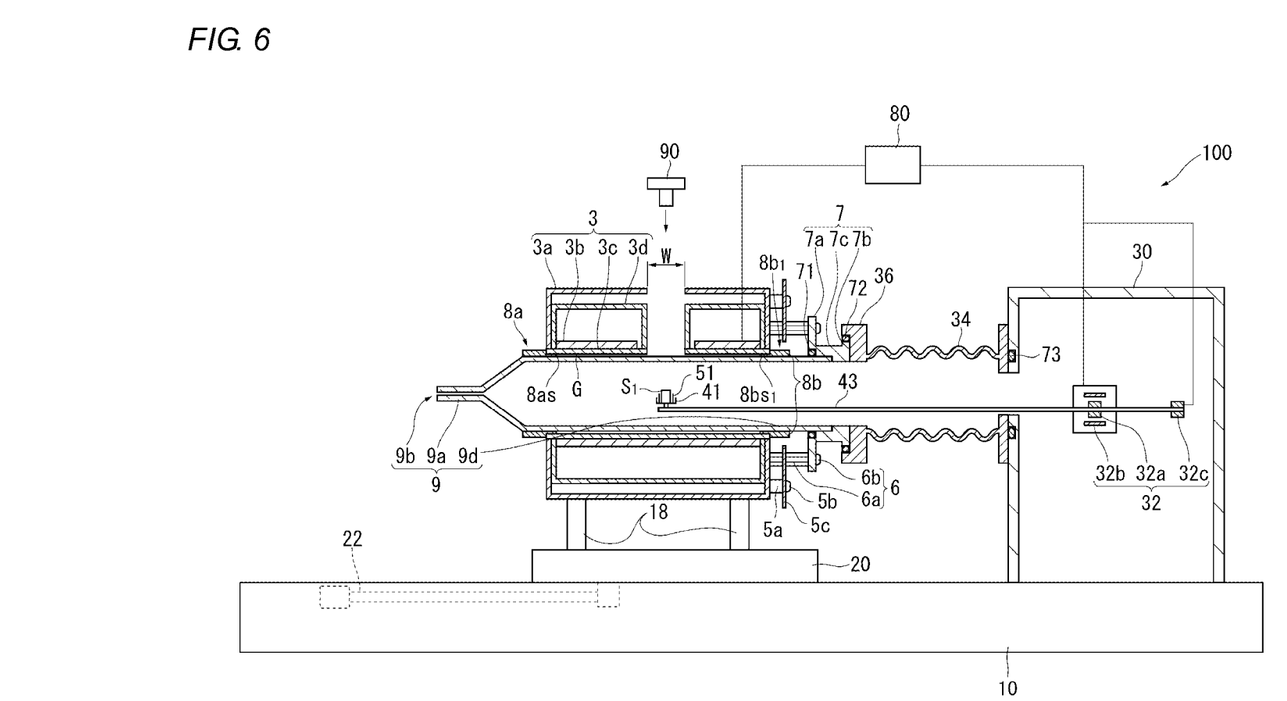
FIG. 6 is a cross-sectional view illustrating a state in which the gap jigs are inserted into a gap between the heating furnace and the furnace tube.

However, as described above, in order to make uniform the heat distribution or heat conduction of the furnace tube 9, the furnace tube 9 and the furnace core tube 3c need to be accurately fixed to each other concentrically by allowing the axial centers thereof to match with each other while the gap between the furnace tube 9 and the furnace core tube 3c of the heating furnace 3 in the radial direction is maintained in a predetermined distance G (see FIG. 6).

Here, in this embodiment, the first flange 7a is engaged with the rod 6a while varying (adjusting) the position thereof in the radial direction. That is, as illustrated in FIG. 7A, the maximum diameter d1 of the rod 6a is greater than the diameter d2 of the bolt hole 7h, and the diameter d2 is greater than the diameter d3 of the screw portion of the male screw 6b. The diameter of the head portion of the male screw 6b is greater than d2. Therefore, in a state where the male screw 6b is loosely screwed into the rod 6a via the bolt hole 7h, the screw portion of the male screw 6b moves in the bolt hole 7h in the radial direction such that the position thereof in the radial direction can be adjusted.

Accordingly, as illustrated in FIG. 5A, the furnace tube 9 is inserted from the insertion hole 3h of the rear end side of the heating furnace 3 (the housing 3a), and subsequently, as illustrated in FIG. 5B, gap jigs 8a and 8b are interposed between the furnace core tube 3c and the furnace tube 9 to maintain the gap at the value G Thereafter, when the male screw 6b is properly screwed into the rod 6a via the bolt hole 7h (FIG. 7B), the furnace tube 9 and the furnace core tube 3c can be concentrically fixed to each other by allowing the axial centers thereof to match with each other.

In addition, the outer surface of the gap jig 8a is reduced in diameter in a stepped shape toward the rear end side and has a cylindrical shape in which the inner diameter thereof is substantially the same as the outer diameter of the furnace tube 9 such that the thickness of a reduced diameter portion Bas is substantially the same as the value G. As illustrated in FIG. 6, the reduced diameter portion Bas of the gap jig 8a is inserted into the gap between the furnace core tube 3c and the furnace tube 9 from the front end side of the furnace tube 9.

On the other hand, the outer surface of the gap jig 8b is reduced in diameter in a stepped shape toward the front end side and is configured by jig components 8b1 and 8b2 which are obtained by halving a cylinder of which the inner diameter is substantially the same as the outer diameter of the furnace tube 9, and the thickness of the each of reduced diameter portions 8bs1 and 8bs2 is substantially the same as the value G. As illustrated in FIG. 6, the jig components 8b1 and 8b2 are put into the gap between the furnace core tube 3c and the furnace tube 9 from between the heat shield plate 5c and the first flange 7a and then assembled to each other to form the gap jig 8b, and the reduced diameter portion 8bs (8bs 1 and 8bs2) is inserted into the gap.

After fixing the furnace tube 9 to the heating furnace 3, the gap jigs 8a and 8b are detached and thermal analysis is performed. In addition, before inserting the furnace tube 9 into the heating furnace 3, the jig components 8b1 and 8b2 may be attached to the outer surface of the furnace tube 9 in advance.

Next, the heat shield plate 5c will be described with reference to FIG. 4. The heat shield plate 5c is made of, for example, a stainless steel plate and suppresses the dissipation of heat in the furnace tube 9 from the rear end side of the housing 3a.

The heat shield plate 5c has an annular shape which has an insertion hole 5h through which the furnace tube 9 is inserted, surrounds the periphery of the furnace tube 9, and extends outward in the radial direction from (the circumference of) the rods 6a. At three positions of the heat shield plate 5c respectively corresponding to the rods 6a, rod insertion holes 5c1 are formed.

In addition, bolt holes (not illustrated) are formed at two points other than the rod insertion hole 5c1 of the heat shield plate 5c, and bolts 5b are respectively inserted through the bolt holes from the rear end facing surface side of the heat shield plate 5c. To a screw portion 5b1 of the bolt 5b, a collar (cylindrical portion) 5a having a shorter length than that of the screw portion 5b1 is externally fitted such that the front end of the screw portion 5b1 is exposed.

When the rods 6a are respectively inserted through the rod insertion holes 5c1 of the heat shield plate 5c and the screw portions 5b1 are respectively screwed into screw holes 3 as formed in the rear end facing surface of the housing 3a, the heat shield plate 5c is positioned in the axial direction by the collar 5a and is held by the rods 6a.

Accordingly, the heat shield plate 5c can be easily and accurately attached to the rear end side of the heating furnace 3 by using the rods 6a as the guides without being disturbed by the rods 6a.

In addition, in this embodiment, the engagement portion 7a can be engaged with the fixing section 6 at a varying angle with a difference of 120 or more degrees in the radial direction of the furnace tube 9. Specifically, as illustrated in FIG. 4, both the bolt holes 7h and the rods 6a of the engagement portion (first flange) 7a are arranged at equal intervals of 120 degrees in the circumferential direction (the radial direction of the furnace tube 9). Therefore, by adjusting the three different bolt holes 7h to the single rod 6a and fixing the two to each other, the flange 7 and the furnace tube 9 can be engaged with (fixed to) the rod 6a at a varying angle with a difference of 120 degrees in the radial direction.

Therefore, in a case where a portion of the furnace tube 9 corresponding to the opening W is deteriorated in clarity but a portion thereof around the opening W is kept clear and transparent and is thus usable, instead of replacing the furnace tube 9, first, the engagement portion 7a is detached from the rod 6a and the furnace tube 9 is rotated by 120 degrees to allow the engagement portion 7a to be attached to the rod 6a with the male screw 6b. Accordingly, a surface of the furnace tube 9, which is clear and transparent can be arranged immediately below the opening W so as to be re-used. Therefore, a single furnace tube can be re-used three times at most, resulting in a reduction in the number of replacing operations and a reduction in cost. Particularly, in a case where the furnace tube 9 is made of YAG ceramic and is thus relatively expensive, the effect of reducing the number of replacing operations is great.

Therefore, a single furnace tube can be re-used three times at most, resulting in a reduction in the number of replacing operations and a reduction in cost. Particularly, in a case where the furnace tube 9 is made of YAG ceramic and is thus relatively expensive, the effect of reducing the number of replacing operations is great.

When the furnace tube 9 is rotated as described above, by interposing the above-mentioned gap jigs 8a and 8b between the furnace core tube 3c and the furnace tube 9, the furnace tube 9 can be reliably re-fixed in a state where the axial centers of the furnace core tube 3c and the furnace tube 9 match with each other.

In addition, although the rotational angle of the furnace tube 9 is 120 degrees in the above example, in a case where the rotational angle is less than 90 degrees, even when the furnace tube 9 is rotated, there is a high possibility that the portion deteriorated in clarity may remain in the opening W. Therefore, the rotational angle is maintained at "90 or more degrees".

In addition, a configuration in which the engagement portion 7a is engaged with the fixing section 6 at a varying angle with a difference of 90 or more degrees in the radial direction of the furnace tube 9 is not limited to the above-described embodiment.

Figure 11:
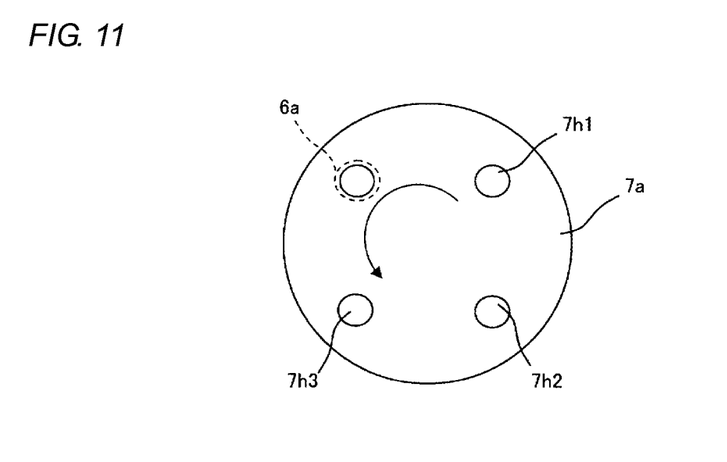
FIG. 11 is a view illustrating a modification example of the structures of the engagement portion and the fixing section.

For example, as illustrated in FIG. 11, when both of the bolt holes 7h of the engagement portion (the first flange) 7a and the rods 6a are arranged at equal intervals of 90 degrees in the circumferential direction (the radial direction of the furnace tube 9) and the adjacent bolt holes 7h1 and 7h2 are interchangeably fixed to the single rod 6a, the furnace tube 9 can be engaged (fixed) at different angles with a difference of 90 degrees. When two bolt holes 7h1 and 7h3 with two bolt holes interposed therebetween are interchangeably fixed to the single rod 6a, the furnace tube 9 can be engaged (fixed) at different angles with a difference of 180 degrees (90 or more degrees) in the radial direction.

Figure 12:
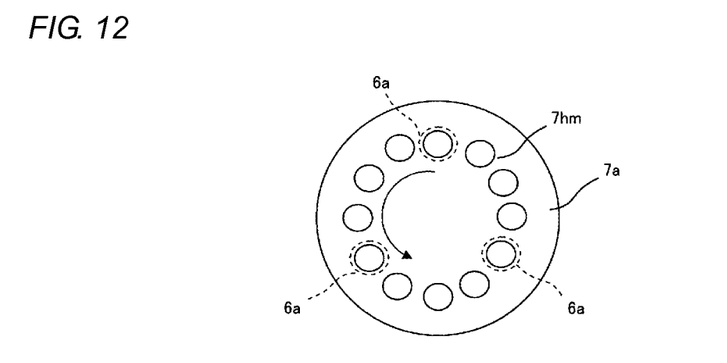
FIG. 12 is a view illustrating another modification example of the structures of the engagement portion and the fixing section.

As illustrated in FIG. 12, for example, when the rods 6a are arranged at equal intervals of 120 degrees while a number of bolt holes 7hm of the engagement portion (the first flange) 7a are arranged at equal intervals in the circumferential direction and predetermined bolt holes 7hm having different positions are aligned with the single rod 6a to be fixed thereto, the furnace tube 9 can be engaged (fixed) at a substantially arbitrary angle with a difference of 90 or more degrees in the radial direction.

Figure 13:
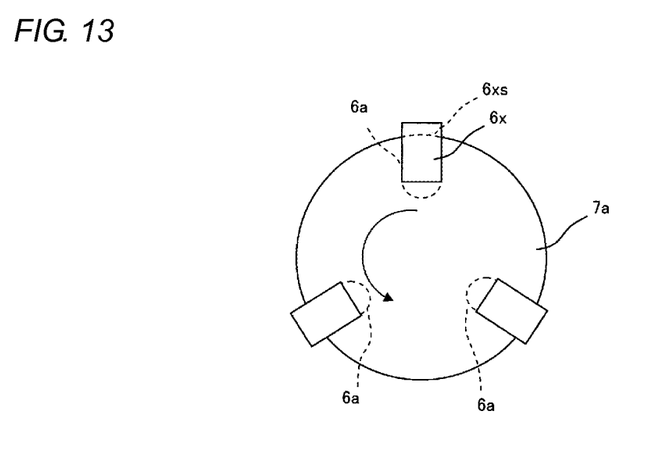
FIG. 13 is a view illustrating still another modification example of the structures of the engagement portion and the fixing section.

As illustrated in FIG. 13, for example, by arranging the rods 6a at equal intervals of 120 degrees in the circumferential direction and attaching interposition portions 6x, which interpose the plate surfaces of the first flange 7a between the front and the rear, to the front ends of the rods 6a, bolt holes may not be provided in the first flange 7a. In addition, when the interposition portion 6x is loosened to rotate the first flange 7a at an arbitrary angle of 90 or more degrees and thereafter the interposition portion 6x is fastened, the furnace tube 9 can be engaged and fixed at a completely arbitrary angle with a difference of 90 or more degrees in the radial direction.

When a positioning portion 6xs which abuts the outer edge of the first flange 7a is formed in the interposition portion 6x, the positioning portion 6xs acts as a guide for rotating the first flange 7a (and the furnace tube 9) around the axial center thereof.

An angle at which the furnace tube 9 is rotated may not be constant.

For example, in the case of a structure illustrated in FIG. 11, after the furnace tube 9 is rotated by 120 degrees as an angle of equal to or larger than 90 degrees so as to be re-used, the furnace tube 9 may be rotated by 240 degrees so as to be re-used and replaced.

Figure 14:
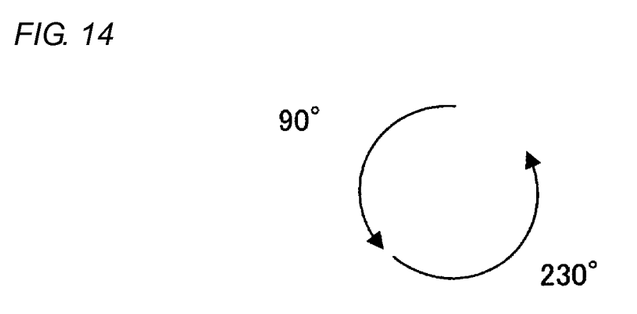
FIG. 14 is a view illustrating an example in which the furnace tube is rotated at a varying angle so as to be re-used.

Otherwise, for example, as illustrated in FIG. 14, in the case of the structures illustrated in FIGS. 12 and 13, after the furnace tube 9 is initially rotated by 90 degrees so as to be re-used, the furnace tube 9 may be rotated by 230 degrees so as to be re-used and replaced. The rotational angle of the furnace tube 9 may be appropriately determined depending on the size of the portion of the furnace tube 9 which is deteriorated in clarity and an attachment angle allowed by the engagement portion 7a and fixing section 6.

Next, a thermal analyzer according to a second embodiment of the present invention will be described with reference to FIG. 8. In addition, FIG. 2 is a cross-sectional view of a thermal analyzer 150 along the axial direction thereof.

The thermal analyzer 150 according to the second embodiment is the same as the thermal analyzer according to the first embodiment except that the gap jigs 8a and 8b are not included, and instead, the furnace core tube 3c of the heating furnace 3 has protrusions 3f.

Figure 8:
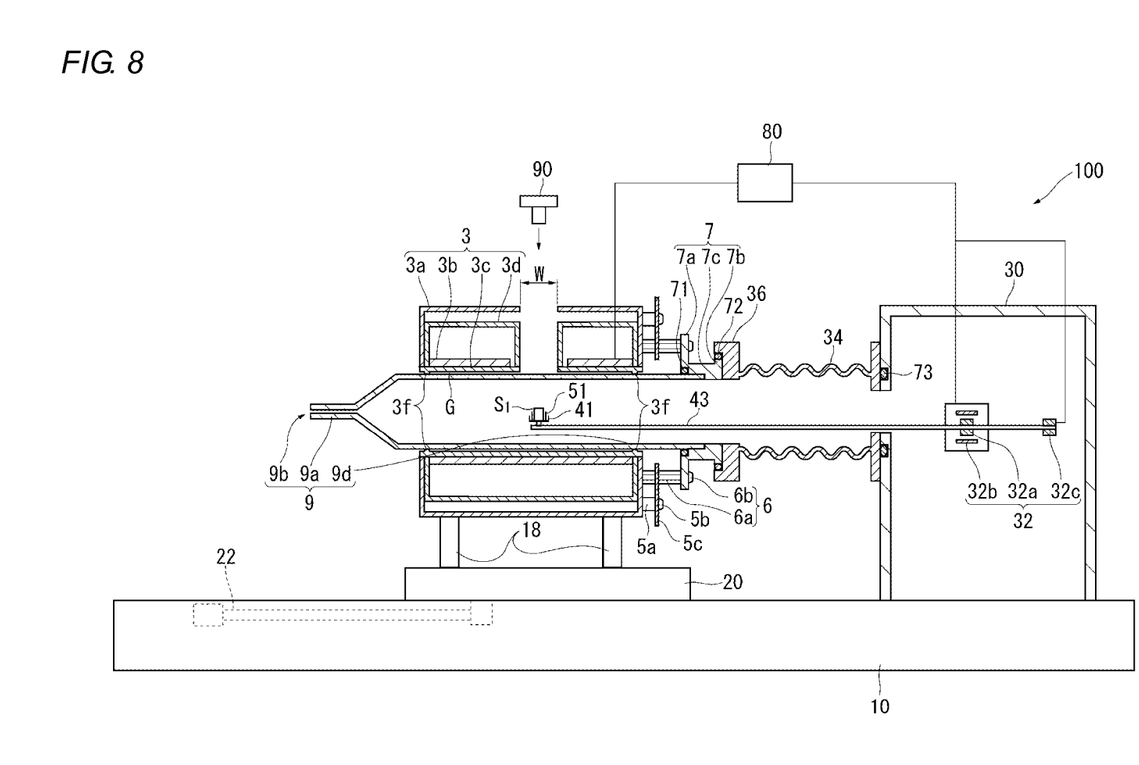
FIG. 8 is a cross-sectional view along an axial direction of a thermal analyzer according to a second embodiment of the present invention.

As illustrated in FIG. 8, protrusions 3f which protrude in the radial direction to a height G are formed at a plurality of points on the inner surface of the front end side and the rear end side of the furnace core tube 3c.

When the furnace tube 9 is inserted into the heating furnace 3, the protrusions 3f come into contact with the outer surface of the furnace tube 9 and thus the gap between the furnace core tube 3c and the furnace tube 9 is adjusted to the value G. In this state, the male screw 6b is properly screwed into the rod 6a via the bolt hole 7h (FIG. 7B). Accordingly, the gap between the furnace core tube 3c and the furnace tube 9 is maintained at the value G, and thus the furnace tube 9 and the furnace core tube 3c can be concentrically fixed to each other by allowing the axial centers thereof to match with each other.

It is preferable that the furnace core tube 3c is made of ceramic such as alumina or quartz. In addition, for example, it is preferable that the protrusions 3f are molded on the inner surfaces of the front end side and the rear end side of the furnace core tube 3c integrally with the furnace core tube at several (in this example, three) positions with equal intervals therebetween on the same circumference. Since stress is applied to the protrusions 3f during insertion and extraction accompanied by the replacement of the furnace tube or during heating, the strength of the protrusions 3f is enhanced by being formed integrally with the furnace core tube.

Here, the protrusions 3f may also be formed by screwing screws made of ceramics into screw holes provided in the inner surfaces of the front end side and the rear end side of the furnace core tube 3c at several (in this example, three) positions with equal intervals therebetween on the same circumference.

It is natural that the present invention is not limited to the above-described embodiment and covers various modifications and equivalents included in the spirit and scope of the present invention.

For example, the configurations, the arrangement states, and the like of the furnace tube and the heating furnace are not limited to those in the above examples. In addition, the shapes, the numbers, and the like of the fixing section, the engagement portion, the gap jigs, and the protrusions are not limited to those in the above examples.

The materials used in the fixing section, the engagement portion, and the gap jigs may be, for example, stainless steel, Cr-coated steel, or the like.

The thermal analyzer of the present invention can be applied to, as well as the above-described thermogravimetry (TG) apparatus, any of thermal analysis methods which are defined in "General rules for thermal analysis" of JIS K 0129:2005 and are used to, when the temperature of a measurement object (sample) is controlled according to programs, measure physical properties of the sample. Specifically, the thermal analysis methods include (1) differential thermal analysis (DTA) for temperature (temperature difference) detection, (2) differential scanning calorimetry (DSC) for thermal flow difference detection, (3) thermogravimetry (TG) for mass (weight change) detection, and the like.

What is claimed is:

1. A thermal analyzer comprising:
   a furnace tube made of a transparent material in a cylindrical shape, the furnace tube having an outlet on an anterior end portion thereof in an axial direction;
   a sample holder that is arranged in the furnace tube and comprises a mounting face on which a sample container containing a measurement sample is mounted;
   a heating furnace configured to have a cylindrical shape and to surround the furnace tube from outside;
   a measurement chamber connected air-tight to the furnace tube at a posterior end portion of the furnace tube in the axial direction;
   a measurement unit arranged inside the measurement chamber and configured to measure changes in physical properties of the measurement sample; and
   a first gap jig and a second gap jig configured to maintain a gap between the heating furnace and the furnace tube in a radial direction in a predetermined distance,
   wherein the heating furnace comprises a fixing section to be fixed to the furnace tube,
   wherein the furnace tube is configured to be attachable to and detachable from the heating furnace,
   wherein the furnace tube comprises an engagement portion that is configured to be engaged with the fixing section at a variable position in the radial direction, and
   wherein the first gap jig and a second gap jig are configured to be detachable from the heating furnace and the furnace tube in a case that the furnace tube is inserted into the heating furnace and the fixing section engages with the engagement portion of the furnace tube while the first gap jig and a second gap jig are interposed between the heating furnace and the furnace tube at a front end side and at a rear end side of the furnace tube to maintain the gap between the heating furnace and the furnace tube in the radial direction in the predetermined distance.

2. The thermal analyzer according to claim 1 further comprising:
   a heat shield plate having an annular shape and configured to surround a periphery of the furnace tube, wherein the fixing section comprises a plurality of rods that extend toward a rear end side from the heating furnace and are arranged at positions surrounding the periphery of the furnace tube on a side further inward in the radial direction than an outer circumference of the heat shield plate, wherein the engagement portion is configured to have an annular shape that surrounds the periphery of the furnace tube and to extend outward in the radial direction from the rods, and a front end facing surface that engages with a rear end facing surface of the rod by being in contact with the rear end facing surface of the rod, and wherein the heat shield plate is configured to be inserted into the rod and held by the rod at a position closer to a front end side of the heating furnace.

3. The thermal analyzer according to claim 1, wherein the furnace tube is made of a material selected from quartz glass, sapphire glass, and YAG ceramic.

4. The thermal analyzer according to claim 1, wherein the engagement portion is configured to be engaged with the fixing section at a variable angle of 90 degrees or more in the radial direction of the furnace tube.

5. A thermal analyzer comprising:
a furnace tube made of a transparent material in a cylindrical shape, the furnace tube having an outlet on an anterior end portion thereof in an axial direction;
a sample holder that is arranged in the furnace tube and comprises a mounting face on which a sample container containing a measurement sample is mounted;
a heating furnace configured to have a cylindrical shape and to surround the furnace tube from outside;
a measurement chamber connected air-tight to the furnace tube at a posterior end portion of the furnace tube in the axial direction; and
a measurement unit arranged inside the measurement chamber and configured to measure changes in physical properties of the measurement sample, wherein the heating furnace comprises a fixing section to be fixed to the furnace tube, wherein the furnace tube comprises, on an inner surface of the heating furnace, protrusions configured to maintain a gap between the heating furnace and the furnace tube in a radial direction in a predetermined distance and to regulate relative position between the heating furnace and the furnace tube by being in contact with the furnace tube, wherein the furnace tube comprises an engagement portion that is configured to be engaged with the fixing section at a variable position in the radial direction, and wherein the engagement portion is configured to be engaged with the fixing section in a case that the furnace tube is inserted into the heating furnace and the protrusions of the heating furnace are brought into contact with an outer surface of the furnace tube to maintain the gap between the heating furnace and the furnace tube in the radial direction in the predetermined distance.

6. The thermal analyzer according to claim 5 further comprising:
a heat shield plate having an annular shape and configured to surround a periphery of the furnace tube, wherein the fixing section comprises a plurality of rods that extend toward a rear end side from the heating furnace and are arranged at positions surrounding the periphery of the furnace tube on a side further inward in the radial direction than an outer circumference of the heat shield plate, wherein the engagement portion is configured to have an annular shape that surrounds the periphery of the furnace tube and to extend outward in the radial direction from the rods, and a front end facing surface that engages with a rear end facing surface of the rod by being in contact with the rear end facing surface of the rod, and wherein the heat shield plate is configured to be inserted into the rod and held by the rod at a position closer to a front end side of the heating furnace.

7. The thermal analyzer according to claim 5, wherein the furnace tube is made of a material selected from quartz glass, sapphire glass, and YAG ceramic.

8. The thermal analyzer according to claim 5, wherein the engagement portion is configured to be engaged with the fixing section at a variable angle of 90 degrees or more in the radial direction of the furnace tube.

* * * * *